(12) United States Patent
Rasmussen

(10) Patent No.: US 6,755,190 B2
(45) Date of Patent: Jun. 29, 2004

(54) INHALER

(75) Inventor: Jörgen Rasmussen, Struer (DK)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 10/221,709

(22) PCT Filed: Mar. 16, 2001

(86) PCT No.: PCT/SE01/00557
§ 371 (c)(1),
(2), (4) Date: Dec. 18, 2002

(87) PCT Pub. No.: WO01/70313
PCT Pub. Date: Sep. 27, 2001

(65) Prior Publication Data
US 2003/0178021 A1 Sep. 25, 2003

(30) Foreign Application Priority Data
Mar. 18, 2000 (GB) .............................................. 0006525

(51) Int. Cl.[7] .......................................... A61M 11/00
(52) U.S. Cl. ............................. 128/200.23; 128/200.14
(58) Field of Search .................. 128/200.14–200.24, 128/203.12, 207.14–207.18; 604/58–60, 94.01

(56) References Cited

U.S. PATENT DOCUMENTS 5,826,571 A * 10/1998 Casper et al. .......... 128/200.23
6,405,727 B1 * 6/2002 MacMichael et al. ... 128/203.12

FOREIGN PATENT DOCUMENTS

| WO | WO 99/49916 | 10/1999 |
|---|---|---|
| WO | WO 00/16835 | 3/2000 |
| WO | WO 00/16838 | 3/2000 |

* cited by examiner

Primary Examiner—Glenn K. Dawson
(74) Attorney, Agent, or Firm—Fish & Richardson P.C.

(57) ABSTRACT

An inhaler for delivery of medicament from a canister which is compressible to deliver a dose of medicament, the inhaler comprises: a housing for holding a canister; a canister engagement member engageable with a canister held in the housing to compress the canister; a loading mechanism for loading a resilient loading element which is arranged, when loaded, to bias the canister engagement member to compress the canister; a triggering mechanism arranged to hold the canister engagement member against compression of the canister and triggerable to release the canister engagement member, and a linkage between the resilient loading element and the canister engagement member, wherein the linkage between the resilient loading element and the canister engagement member is arranged to reduce the force applied by the canister engagement member to the triggering mechanism when held by the triggering mechanism.

18 Claims, 14 Drawing Sheets

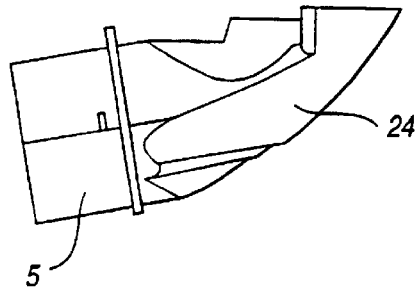
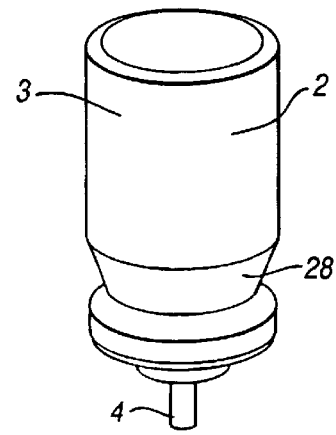
Fig.3
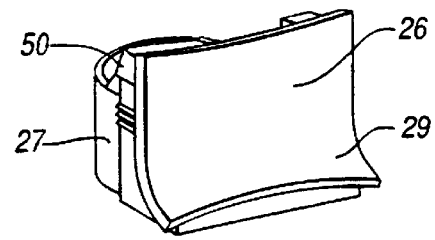
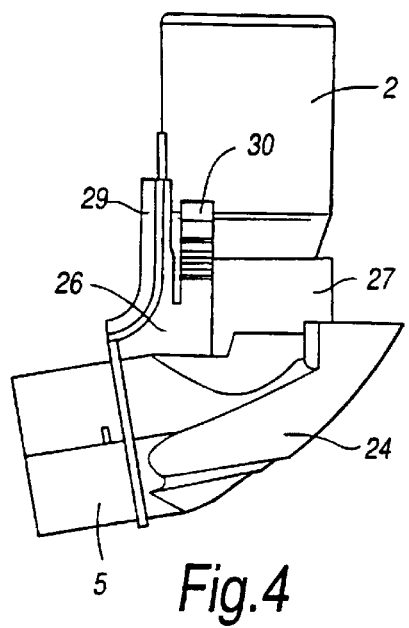
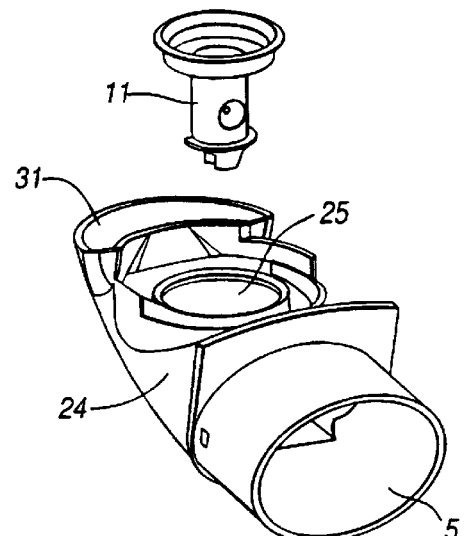
Fig.4    Fig.5

INHALER

CROSS REFERENCE TO RELATED APPLICATIONS

The present application is a national phase application under 35 U.S.C. Section 371 filed from International Patent Application PCT/SE01/00557 filed Mar. 16, 2001, which claims priority to United Kingdom patent application Serial. No. 0006525.0, filed Mar. 18, 2000. The contents of these applications are incorporated herein by reference in their entirety.

BACKGROUND OF THE INVENTION

The present application relates to an inhaler for delivery of medicament from a canister, in particular to an actuation mechanism for actuating the canister held in the inhaler.

Inhalers are commonly used to deliver a wide range of medicaments. The inhaler holds a canister of medicament which is actuatable, for example by compression, to deliver a dose of medicament. Some known inhalers are provided with an actuation mechanism for actuating the canister. The mechanism may be breath-actuated, ie. arranged to actuate the canister in response to inhalation at the mouthpiece. Typically a breath-actuated inhaler includes a loading mechanism for loading a resilient loading element with an actuation force for compression of the canister. A triggering mechanism may be provided to hold the resilient loading element against compression of the canister, the triggering mechanism releasing the resilient loading element upon inhalation.

In such an actuation mechanism the resilient loading element must provide a sufficiently high force to compress the canister. In general, the force generated by a resilient loading element decreases as it expands during the compression stroke of the canister. For example if the resilient loading element is a spring, the force generated will decrease linearly with the expansion of the spring in proportion to its spring constant. Therefore, to provide sufficient force at the end of the compression stroke of the canister, the force generated by the resilient loading element at the beginning of the stroke is larger still. This is the loaded position in which the actuation mechanism will usually be stored, ready for use.

However, it is undesirable to store the actuation mechanism with the resilient loading element applying a high force to the other elements holding the loading element in its loaded position, such as the triggering mechanism. This is because the high force can cause creep in the various components subject to the high force, particularly if the components are made of plastic which is desirable to reduce costs and simplify manufacture. Over time such creep can distort the components of the actuation mechanism. This can have the effect of causing improper actuation of the canister, for example by causing actuation at an incorrect inhalation flow or, in the worst case, preventing operation of the actuation mechanism at all.

SUMMARY OF THE INVENTION

According to the present invention, there is provided an inhaler for delivery of medicament from a canister which is compressible to deliver a dose of medicament, the inhaler comprising:

a housing for holding a canister;

a canister engagement member engageable with a canister held in the housing to compress the canister;

a loading mechanism for loading a resilient loading element which is arranged, when loaded, to bias the canister engagement member to compress the canister;

a triggering mechanism arranged to hold the canister engagement member against compression of the canister and triggerable to release the canister engagement member, wherein the linkage between the resilient loading element and the canister engagement member is arranged to reduce the force applied by the canister engagement member to the triggering mechanism when held by the triggering mechanism.

The present invention is based on the appreciation that it is possible to arrange the linkage between the resilient loading element and the canister engagement member to reduce the force above other canister engagement members and to the triggering mechanism in the loaded state. There are many different ways of arranging the linkage to achieve this.

DESCRIPTION OF DRAWINGS

To allow better understanding, an inhaler which embodies the present invention will now be described by way of non-limitative example with reference to the accompanying drawings, in which:

FIG. 3 is a side view of the duct;

FIG. 4 is a side view of the canister and duct assembled together;

FIG. 5 is an exploded view of the canister, collar and duct;

DETAILED DESCRIPTION OF THE INVENTION

Figure 1:
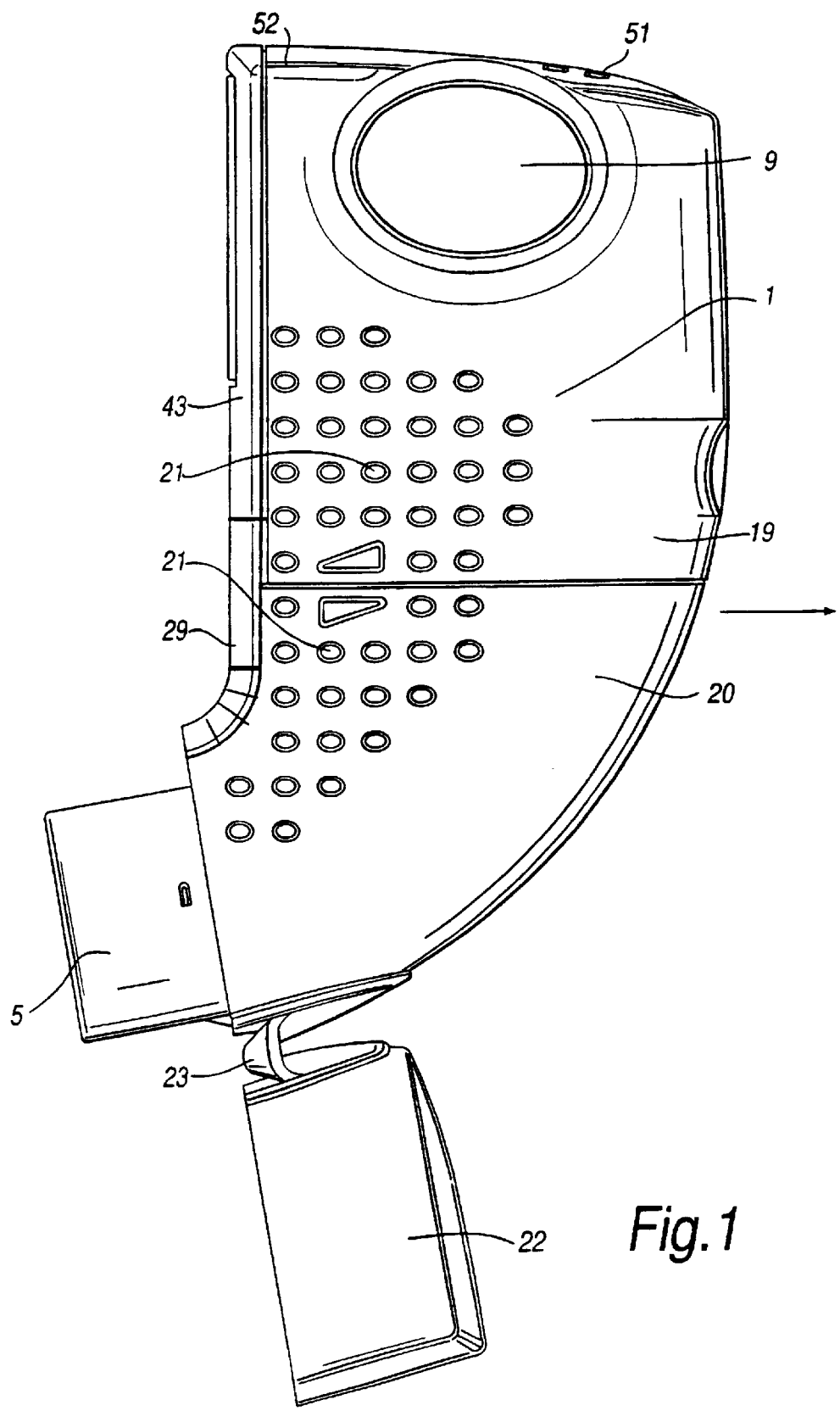
FIG. 1 is a side view of the inhaler.

As illustrated in FIG. 1, the inhaler has a housing 1 comprising an upper portion 19 and a lower portion 20. As illustrated in the cross-sectional view of FIG. 2, the upper housing portion 19 is a hollow shell which holds a canister 2 of medicament having a generally cylindrical body 3 held with its axis in a predetermined direction, vertical in FIG. 2. The upper housing portion 19 houses an actuation mechanism for actuating the canister 2 which will be described in more detail below.

The interior of the upper housing portion 19 is open to the atmosphere by means of air inlets 51 formed in the upper wall 52 of the upper housing portion 19. The location of the air inlets 51 minimises occlusion by the users hand which will normally grip the sides of the housing 1 and not cover the upper wall 52.

The canister 2 is compressible to deliver a dose of medicament. In particular the canister 2 has a valve stem 4 which is compressible relative to the body 3 to deliver a dose of medicament from the valve stem 4. The canister is of a known type including a metering chamber which captures a defined volume the medicament from the body 3 of the canister 2. This volume of medicament is delivered as a metered dose from the valve stem 4 on compression of the valve stem 4 relative to the body 3. The valve stem 4 is weakly biassed outwardly by an internal valve spring (not shown) to reset the canister 2 after compression for refilling the metering chamber.

The lower housing portion 20 is a hollow shell connected to the upper housing portion 19 by a sliding joint (not shown) which allows the lower portion 20 to be separated in the direction of the arrow in FIG. 1 by the user gripping textured surfaces 21 formed on the upper and lower housing portions 19 and 20. A cap 22 is hinged to the lower housing portion 20 by a flexible joint 23 to cover and uncover a mouthpiece 5 protruding from the lower housing portion 20.

Figure 2:
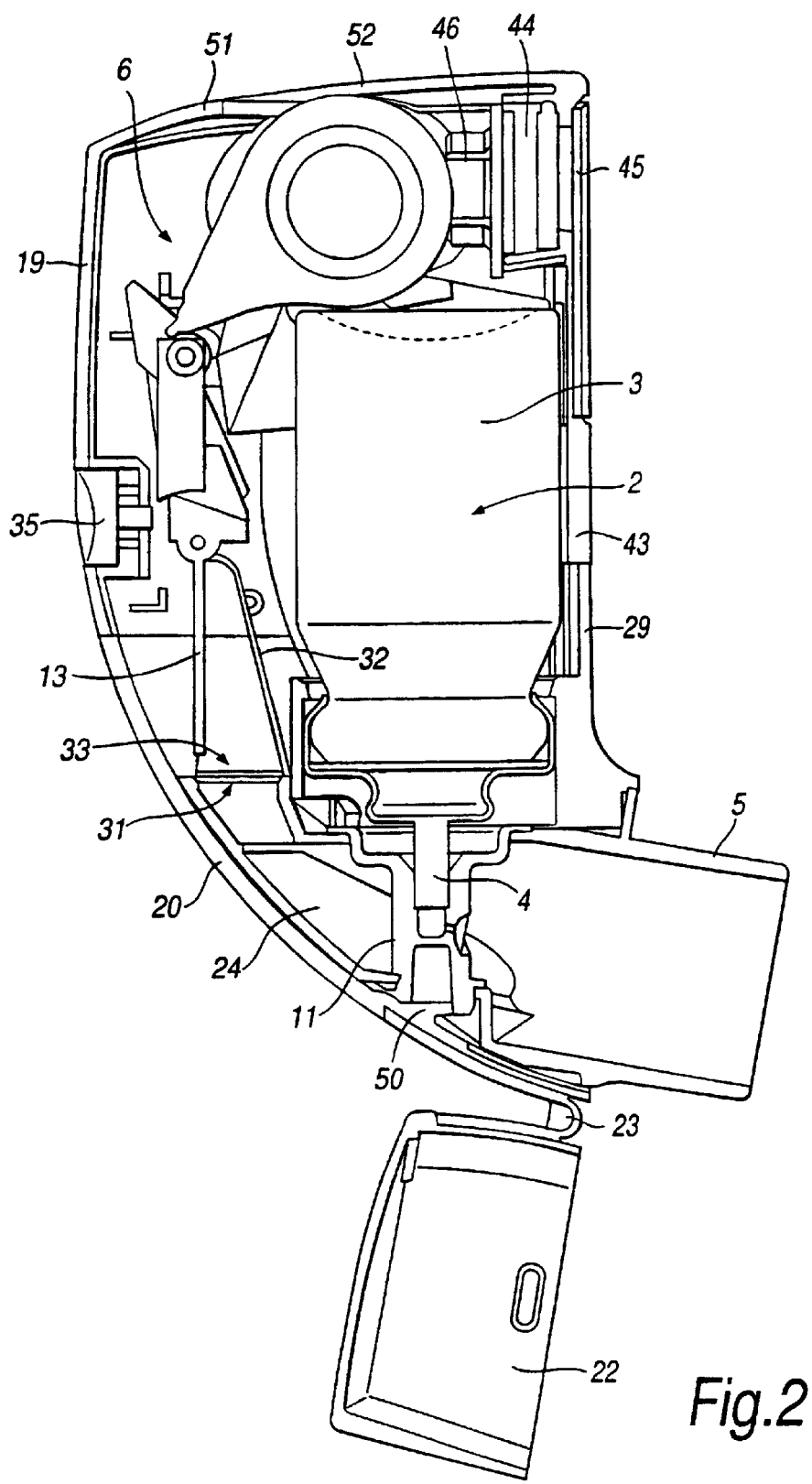
FIG. 2 is a cross-sectional view of the inhaler illustrating the housing and duct.

As shown in FIG. 2, the lower housing portion 20 houses a duct 24 which is integrally formed with the mouthpiece 5, as illustrated in isolation in FIG. 3.

Figure 6:
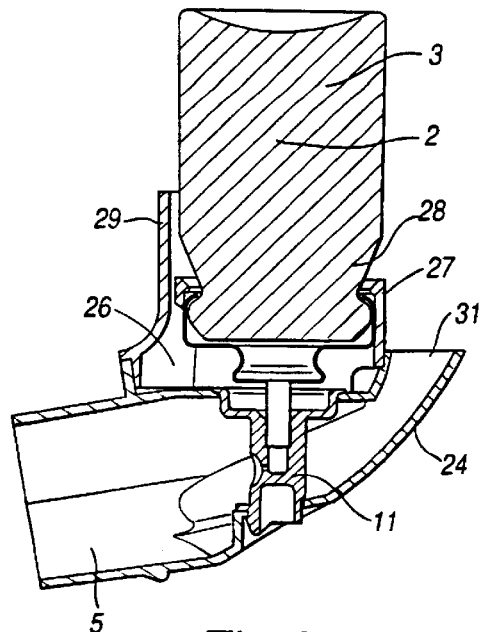
FIG. 6 is a cross-sectional view of the canister and dust assembled together.

The duct 24 is assembled with a canister 2 as shown in FIGS. 4 to 6. The duct 24 receives a nozzle block 11 in an opening 25. The valve stem 4 of the canister is received in the nozzle block 11 which is arranged to direct a dose of medicament delivered from the valve stem 4 out of the inhaler through the mouthpiece 5. The duct 24 and nozzle block 11 are separately formed. This allows each to be manufactured and subsequently assembled. This produces manufacturing and logistical savings because it facilitates different nozzle block designs being incorporated with a single duct design and vice versa.

A collar 26 is permanently connected to the canister 2. The collar 26 includes an annular retaining ring 27 permanently fitted around a necked portion 28 of the canister body 3. The retaining portion 27 prevents removal of the collar 26 from the canister such that the collar 26 is removed and replaced together with the canister 2. However, the retaining portion 27 and the canister 2 have a small degree of relative movement along the axis of the canister 5 to allow compression of the canister body 2 towards the valve stem 4.

The collar 26 further includes a front panel 29 integrally formed with the retaining ring 27. When the canister 2 is inserted in the housing 1, the front panel 29 of the collar 26 closes an opening formed between the upper housing portion 19 and the lower portion 20 and therefore forms a part of the outer wall of the housing 1. Accordingly, the presence or absence of the front panel 29 provides a visual indication to the user of whether or not a canister 2 has been inserted in the canister, because the collar 26 is permanently connected to the canister 2.

A pair of catch arms 30 integrally formed with the front panel 29 of the sides of the collar 26 catch the interior surface of the upper housing portion 19 to hold the collar 26 and the canister 2 in the upper housing portion 19.

The lower housing portion 20 has a stud 50 which locates the end of the nozzle block 11 as shown in FIG. 2 to hold the lower housing portion 20 and the duct 24 in place relative to one another. However, the lower housing portion 20 is not retained on the duct 24, so may be removed from the upper housing portion 19 leaving the canister 2 inserted in the upper housing portion 19 and the duct 24 held on the canister 2 by the valve stem 4 being inserted in the nozzle block 11. The duct 24 and nozzle block 11 may subsequently be slid off the valve stem 4 for cleaning or replacement. The canister 2 and collar 26 may be slid out from the upper housing portion 19 after depression of the catch arms 30. Subsequently a replacement canister 2 and collar 26 may be inserted.

Typically a new duct 24 and nozzle block 11 will be provided to the user with each new canister 2 so that the duct 24 and mouthpiece 5 are regularly replaced to prevent damage or dirt building up over time. The duct 24 has an opening 31 at its end opposite from the mouthpiece 5.

As shown in FIG. 2, the upper housing portion 19 holds a flap duct 32 which extends from a flow inlet 33 to a flap 13 which forms part of the triggering mechanism for the actuation mechanism as described in detail below. Therefore the duct 24 housed in the lower housing portion 19 and the flap duct 32 together define a composite duct shaped to direct the inhalation flow from the mouthpiece 5 to the flap 13. The composite duct formed by the duct 24 and the flap duct 32 is shaped to control the flow to the flap 13 to provide appropriate flow characteristics for proper operation of the flap 13.

The inhaler is further provided with an actuation mechanism 6. To assist understanding, a general description of the overall structure and operation of the actuation mechanism 6 will first be given.

An actuation force for compressing the canister 2 is stored in a resilient loading element in the form of a torsion spring 7. To load the torsion spring 7, the actuation mechanism 6 includes a loading mechanism consisting of a loading member in the form of a rotatable spindle 8 and two contact members in the form of buttons 9 which protrude from the housing as shown in FIG. 1. Depression of the buttons 9 towards one another, relative to the housing 1, drives the loading member 8 to load the torsion spring 7 through a cam arrangement between the buttons 9 and spindle 8.

The torsion spring 7 biasses compression of the canister 2 by engaging a canister engagement member in the form of a lever 10 which depresses the body 3 of the canister towards the stem 4 held in the nozzle block 11.

To allow storage of the actuation force in the torsion spring 7 after loading, the actuation mechanism 6 includes a triggering mechanism. This includes a locking lever 12 which holds the canister engagement lever 10 against compression of the canister 2. To release the canister engagement lever 10, the triggering mechanism further includes a vane in the form of a flap 13 which in a rest state holds the locking lever 12 in place. Inhalation at the mouthpiece 5 moves the flap 13 to release the locking member 12. This in turn releases the canister engagement lever 10 allowing the torsion spring 7 to drive compression of the canister 2.

The actuation mechanism 6 further includes a locking mechanism which locks the spindle 8 after loading of the torsion spring 7, thereby holding the torsion spring 7 in its loaded state before triggering and locking the canister in its compressed state after triggering.

The locking mechanism includes a catch 14 which, in a locking position, catches the spindle 8 and holds the torsion spring 7 in its loaded state. The locking mechanism further includes an intermediate member 15. A resilient biassing element in the form of a spring 16 is provided between the catch 14 and the intermediate member 15 to bias the catch 14 towards its locking position. The spring 16 allows deflection of the catch 14 by the spindle 8 during loading of the torsion spring 7.

Prior to inhalation the intermediate member 15 is held in place by the canister engagement lever 10. Upon inhalation at the mouthpiece 5, the flap 13 engages the intermediate member 15 to hold it in place. After compression by the canister engagement lever 10, the canister 2 is locked in its compressed state by the catch 14 of the locking mechanism holding the spindle 8 in place.

When the level of inhalation at the mouthpiece falls below a predetermined threshold, the flap 13 releases the intermediate member 15 to unload the biassing element 16 which in turn allows the catch 14 to release the spindle 8. After release by the catch 14, the spindle 8, torsion spring 7 and canister engagement lever 10 move upwardly and the canister resets.

Figure 7:
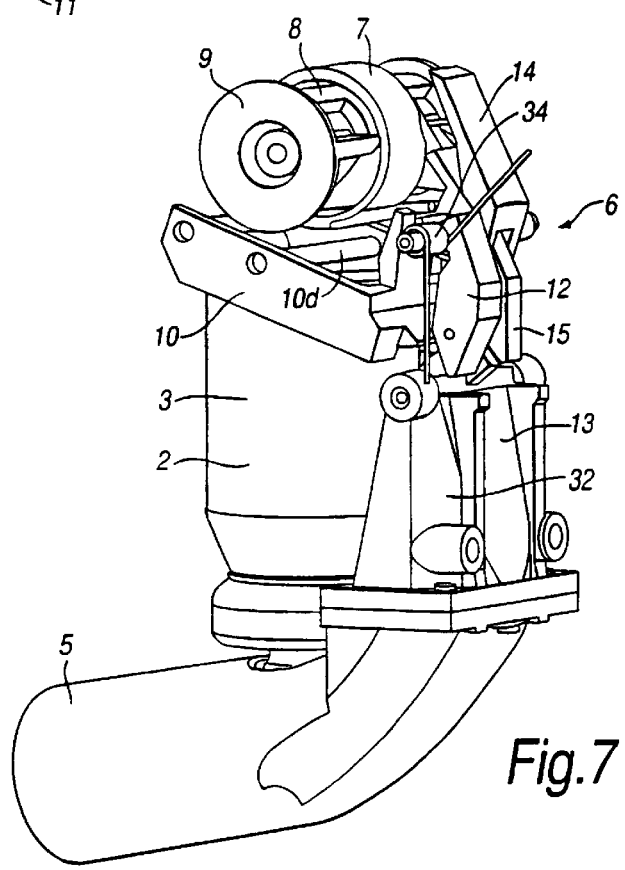
FIG. 7 is a view from the side and rear of the actuation mechanism.

Now there will be given a detailed description of the actuation mechanism 6, the entirety of which is illustrated in FIG. 7 and parts of which are illustrated in FIGS. 8 to 13.

Figure 8:
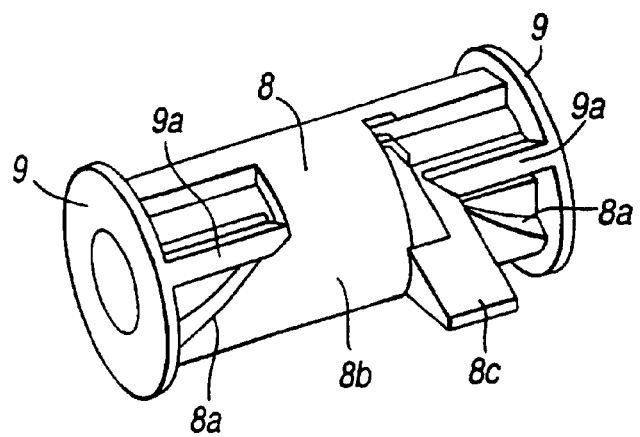
FIG. 8 is a view from the rear of the spindle.

The loading mechanism is illustrated in FIG. 8 and consists of a rotatable spindle 8 and two contact members in the forms of buttons 9 at both ends. The spindle 8 is rotatably mounted in the upper housing portion 19 about an axis orthogonal to the axis of the cylindrical body 3 of the canister 2. The spindle 8 has a pair of cam surfaces 8a disposed on opposite sides of the rotational axis of the spindle 8. The buttons 9 are mounted in the housing to be movable in a movement direction parallel to the rotational axis of the spindle 8. The buttons 9 each have a pair of inwardly projecting cam followers 9a which each engage a respective cam surface 8a of the spindle 8. The cam arrangement of the cam surfaces 8a and the cam followers 9a between the spindle 8 and the buttons 9 causes depression of the buttons 9 to drive rotation of the spindle 8.

Figure 9:
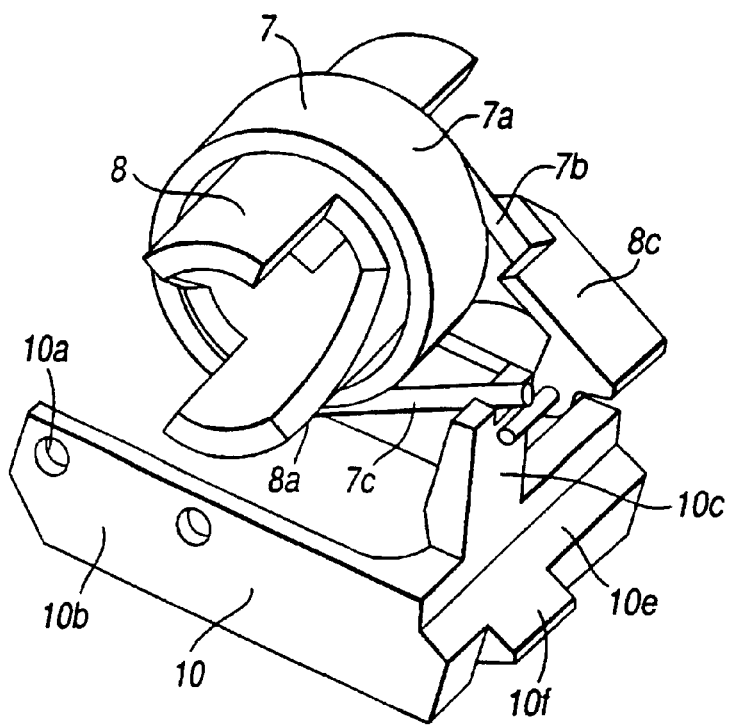
FIG. 9 is a view from the side, rear and above showing the arrangement of the resilient loading element.

As illustrated in FIG. 9, the torsion spring 7 which forms the resilient loading element is disposed with its coils 7a encircling a central cylindrical surface 8b of the spindle 8. A catch arm 8c protrudes radially from the spindle 8. A first leg 7b of the torsion spring 7 is restrained by the catch arm 8c so that the movement of the spindle 8 driven by the buttons 9 loads the torsion spring 7.

Figure 10:
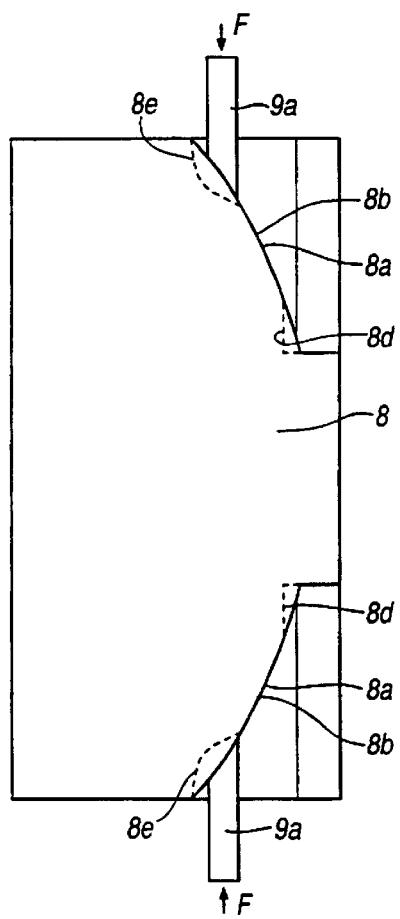
FIG. 10 is a schematic view of the cam surfaces formed on the spindle.

As illustrated schematically in FIG. 10, the cam surfaces 8a have a non-linear shape which causes the gearing ratio of the amount of driven movement of the spindle 8 to the amount of movement of the buttons 9 to be a non-linear function of the rotational position of the spindle 8. The major portion 8b of each cam surface 8a is shaped with increasing pitch to compensate for the increased reactive loading force applied by the torsion spring 7 to the spindle 8 as the buttons 9 are depressed. In particular, they are shaped such that the necessary force applied to the buttons is substantially constant so the user feels a linear resistance. As the torsion spring 7 has a linear spring constant, this is achieved by shaping the major portion 8b of each cam surface 8a such that the gearing ratio is inversely proportion to the rotational position of the spindle 8.

Optionally, the outermost portion of the cam surfaces 8a which are contacted by the cam followers 9a during the initial portion of the driven movement of the spindle may have a decreased pitch, for example as illustrated by the dotted lines 8e. This is to reduce the gearing ratio relative to the subsequent major portion 8b. In this way the user initially feels a low resistance to movement of the buttons 9. This improves the feel perceived by the user and also assists the user in applying force.

Another option is to provide the final portion of the cam surface 8a with a detent, for example as illustrated by the dotted lines 8d. When the end of the cam followers 9a reach the detent 8d, the cam surface 8a of the spindle 8 no longer exerts a force urging the buttons outwardly on the buttons 9. At this position the detent 8d is urged by the torsion spring 7 against the side of the cam followers 9a and therefore holds the buttons 9 in their innermost position. This prevents the buttons 9 from loosely sliding back and forth after the torsion spring 7 has been loaded.

As shown in FIG. 9, the torsion spring 7 engages a canister engagement lever 10 which is pivotally mounted to the interior of the housing about an axis 10a. The canister engagement lever 10 is generally U-shaped with two parallel sides 10b connected by a cross piece 10c. A bar 10d extending between the two sides 10b bears on the body 5 of the canister 2. A mount 10e formed on the cross-piece 10c is engaged by the second leg 7c of the torsion spring 7, whereby loading of the torsion spring 7 biasses the lever 10 to compress the canister 2. The canister engagement lever 10 is biassed upwardly by a reset spring (not shown), which may be arranged as a torsion spring on the axis 10a, but this is weaker than the torsion spring 7.

The torsion spring 7, spindle 8 and canister engagement lever 10 are all rotatable about axis orthogonal to the cylindrical axis of the body 5 of the canister 2. This provides a simple and reliable loading mechanism particularly because of the arrangement of the torsion spring 7 with its coils 7a encircling the spindle 8. Some or all of these elements could alternatively be linearly movable in a plane parallel to the cylindrical axis of the body 5 of the canister 2 to achieve a loading mechanism which is equally simple to construct. However rotatable elements are preferred from the point of view of reliability in repeated use of the actuation mechanism 6.

On the other hand, the movement of the buttons in a direction orthogonal to the cylinder axis of the body 3 of the canister 2 assists the user in application of force to the loading mechanism. As typical for inhalers, the housing 1 extends in the direction of the cylindrical axis of the body 3 of the canister 2, so may be easily held in the palm of a hand with the buttons 9 protruding from either side. Thus the buttons 9 are easily depressed between a finger and thumb. Alternatively a single button could be provided allowing loading in a similar manner by the user pressing the button and the housing on the opposite side to the button. Either configuration also allows loading by laying the inhaler on a surface and applying force for example with the palm of a hand. This facilitates loading by a user with limited finger control or movement, for example a chronic arthritis sufferer.

Figure 11:
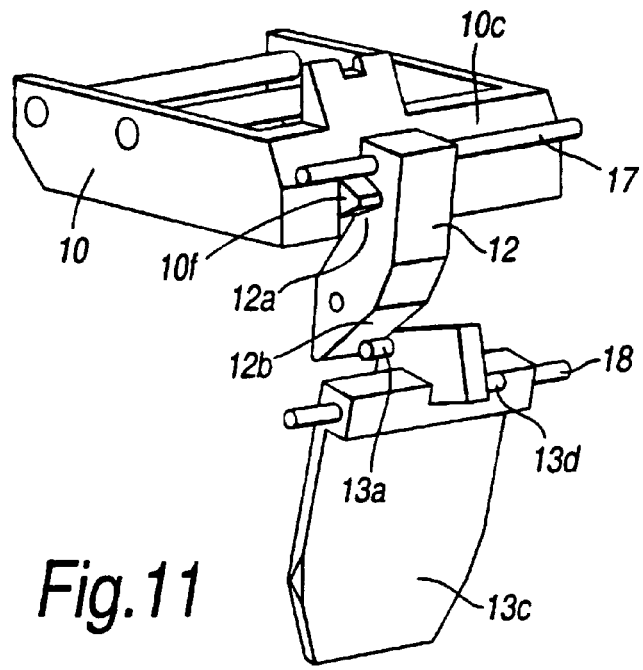
FIG. 11 is a view from the side and rear of the triggering mechanism.
Figure 12:
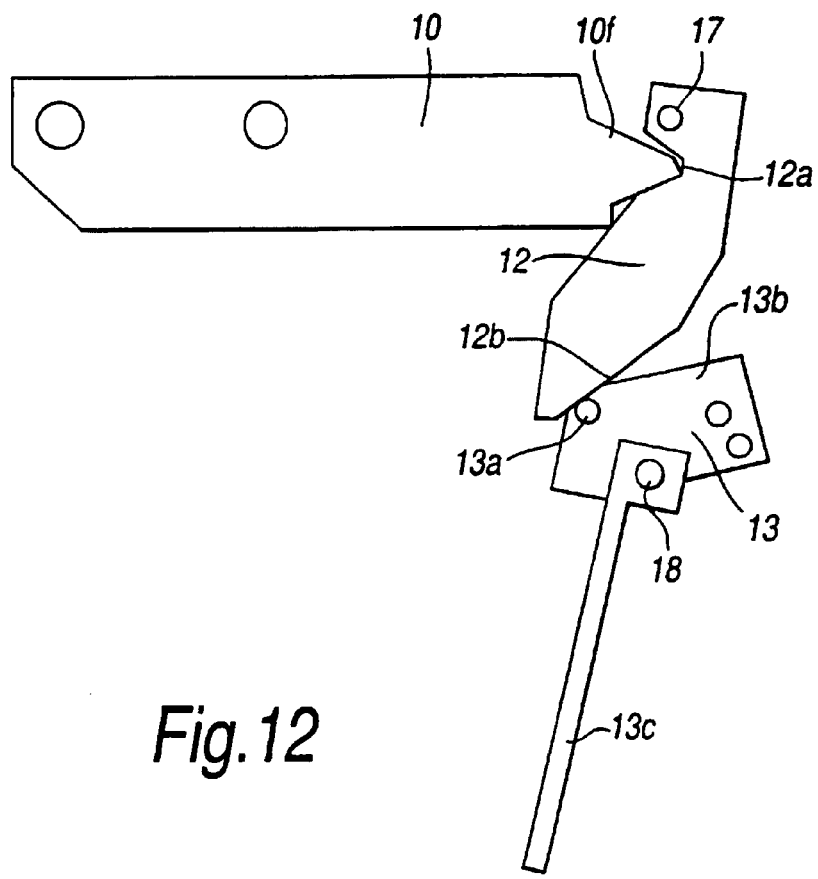
FIG. 12 is a side view of the triggering mechanism.

The actuation member mechanism 6 includes a triggering mechanism as illustrated in FIGS. 11 and 12 which allows storage of the actuation force in the torsion spring 7 after loading.

The triggering mechanism includes a locking lever 12 which is pivotably mounted on an axle 17 extending across the interior of the housing 1. The locking lever 12 has a notch 12a adjacent the axle 17. In a reset state shown in FIG.

12, the notch 12a holds a protrusion 10f protruding from the cross-piece 10c of the canister engagement lever 10, thereby holding the lever 10 against compression of the canister 2. The locking lever 12 is weakly biassed towards the position shown in FIGS. 11 and 12 by a reset spring 34 arranged as a torsion spring on the axle 17.

The triggering mechanism further includes a vane in the form of a flap 13 which is rotatably mounted on an axle 18 extending across the interior of the housing 1. The flap 13 biassed by a reset spring (not shown), which may be arranged as a torsion spring on the axle 18, towards the position shown in FIG. 12. The flap 13 has a locking lever engagement surface 13a which protrudes from a block 13b positioned above the axle 18. In the position shown in FIG. 12, the engagement surface 13a engages a contact surface 12b formed on the end of the locking lever 12 distal from the axle 17 to hold the locking lever 12 in place holding the canister engagement lever 10.

The flap 13 is disposed in the composite duct formed by the duct 24 and the flap duct 32 extending from the mouthpiece 5 with a flap portion 13c extending across the composite duct at the opposite end from the mouthpiece 5, where the duct opens into the interior of the housing 1. Therefore, the flap 13 is responsive to inhalation at the mouthpiece 5.

Inhalation of the mouthpiece draws the flap portion 13c into the flap duct 32 (clockwise in FIG. 2 and anticlockwise in FIG. 12). Such rotation of the flap 13 allows the locking lever engagement surface I 3a to move out of contact with the contact surface 12b of the locking lever 12.

The upper housing portion 19 also mounts a button 35 disposed adjacent the flap 13 above the axle 18 so that depression of the button 35 rotates the flap 13 in the same direction as inhalation at the mouthpiece 5. Therefore, the button 35 allows the actuation mechanism 6 to be manually released without inhalation at the mouthpiece 5, for example to allow actuation of the canister 2 for testing.

When the canister engagement lever 10 is loaded by the torsion spring 7, release of the locking lever 12 by the flap 13 allows the canister engagement lever 10 to be driven to compress the canister 2. The protrusion 10f deflects the locking lever 12 (anticlockwise in FIG. 12) as the canister engagement lever 10 passes.

Figure 13:
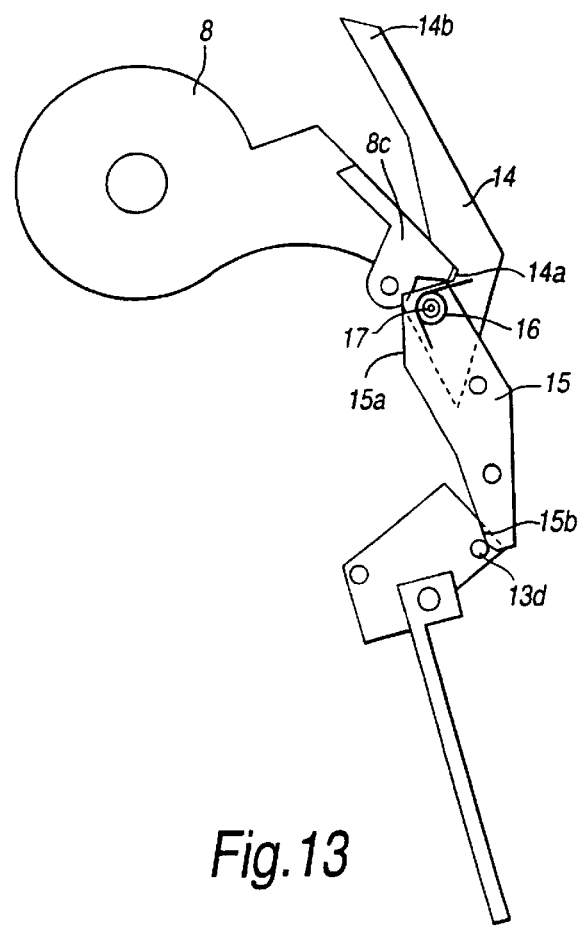
FIG. 13 is a side view of the locking mechanism.

As illustrated in FIG. 13, the actuation mechanism 6 further includes a locking mechanism for locking the spindle 8 after loading of the torsion spring 7. The locking mechanism comprises a catch 14 and an intermediate member 15 which are both pivotally mounted on the axle 17, adjacent the locking lever 12. Before compression of the canister 2, the intermediate member 15 is held in the position illustrated in FIG. 13 by the cross-piece 10c of the canister engagement lever 10 contacting a first contact surface 15a adjacent the axle 17. A resilient biassing element in the form of a torsion spring 16 is connected between the catch 14 and the intermediate member 15 and loaded to bias the catch 14 towards its locking position shown in FIG. 13.

The catch 14 has a notch 14a adjacent the axle 17 for engaging the arm 8c of the spindle 8 after rotation to the position illustrated in FIG. 13 where the torsion spring 7 is loaded. In this position, the loading provided by the spring 16 prevents release of the spindle 8 and thereby holds the torsion spring 7 in its loaded state. Before loading, the arm 8c of the spindle 8 is positioned above the end 14b of the catch 14 distal from the axle 17. When the spindle 8 is driven downwards by depression of the buttons 9, the arm 8c of the spindle engages the end 14b of the catch 14 and deflects the catch 14 by compressing the spring 16 to allow passage of the arm 8c of the spindle 8.

The flap 13 further includes a stud 13d protruding from the block 13b on the opposite side of the axle 18 from the locking lever engagement surface 13a. Upon inhalation at the mouthpiece 5, the flap 13 moves to the position illustrated in FIG. 13 where the stud 13d engages a second contact surface 15b of the intermediate member 15 distal from the axle 17. Prior to this point, the stud 13d does not contact the second contact surface 15b but the intermediate member 15 has been held in place by the canister engagement lever 10. Movement of the flap 13 triggers the triggering mechanism to release the canister engagement member 10 which moves downwards out of contact with the intermediate member 15. However, the stud 13d catches the contact surface 15b and so continues to hold the intermediate member 15 with the spring 16 loaded. Accordingly, the catch 14 remains in its locking position locking the spindle 8 by engagement of the arm 8c of the spindle 8 in the notch 14a of the catch 14.

Subsequently, when the level of inhalation of the mouthpiece falls below a predetermined threshold, the flap moves out of contact with the intermediate member 15 (clockwise in FIG. 13). The level of the predetermined threshold at which the flap 13 releases the intermediate member 15 is controlled by the shape of the second contact surface 15b of the intermediate member 15.

After release by the flap 13, the intermediate member 15 is driven by spring 16 which unloads (clockwise in FIG. 13). Such unloading of the spring 16 reduces the force by which the catch 14 is biassed towards its locking position. Accordingly, the force of the torsion spring 7 acting on the canister engagement lever 10 is sufficient to force the catch arm 8c of the spindle 8 out of the notch 14a. Accordingly, the spindle 8, the torsion spring 7 and canister engagement lever 10 are able to move upwardly biassed by the reset spring acting on the canister engagement lever 10, thereby allowing the canister to reset.

Figures 14A, 14B, 14C, 14D, 14E, 14F:
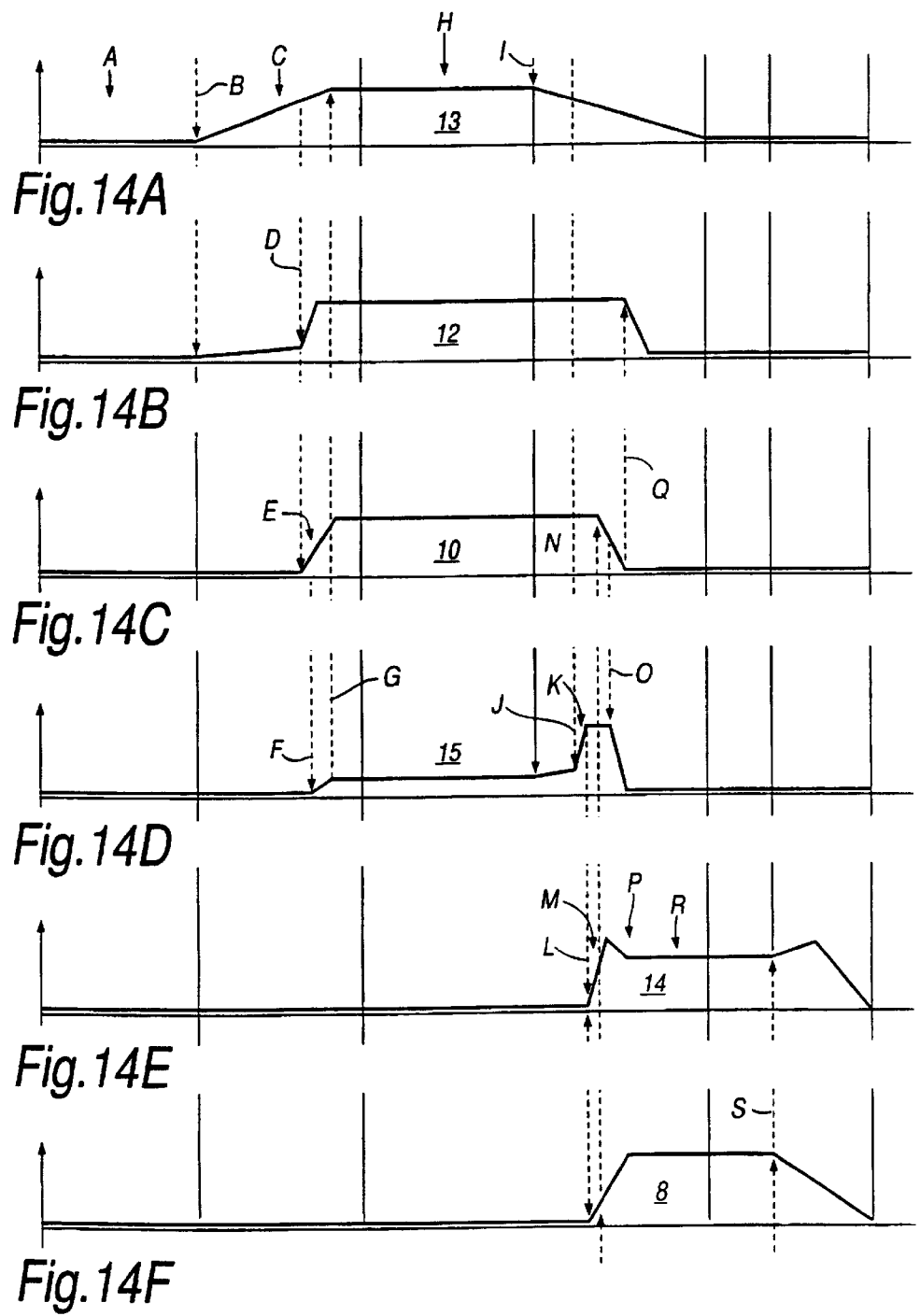
FIGS. 14A to 14F are graphs showing the angular positions of the elements of the actuation mechanism during its operation sequence.

The sequence of operation of the actuation mechanism 6 will now be described with reference to FIGS. 14 to 22. FIGS. 14A to 14F are graphs showing the angular positions of the various elements of the actuation mechanism 6. In particular, FIG. 14A illustrates the angular position of the flap 13; FIG. 14B illustrates the angular position of the locking lever 12; FIG. 14C illustrates the angular position of the canister engagement lever 10; FIG. 14D illustrates the angular position of the intermediate member 15; FIG. 14E illustrates the angular position of the catch 14; and FIG. 14F illustrates the angular position of the spindle 8. Various states and positions of the actuation mechanism 6 are labelled by the letters A to R in FIG. 14 and FIGS. 15 to 22 illustrate the actuation mechanism 6 in some of these states with the views from opposite sides being suffixed by the letters A and B, respectively.

Figure 15A:
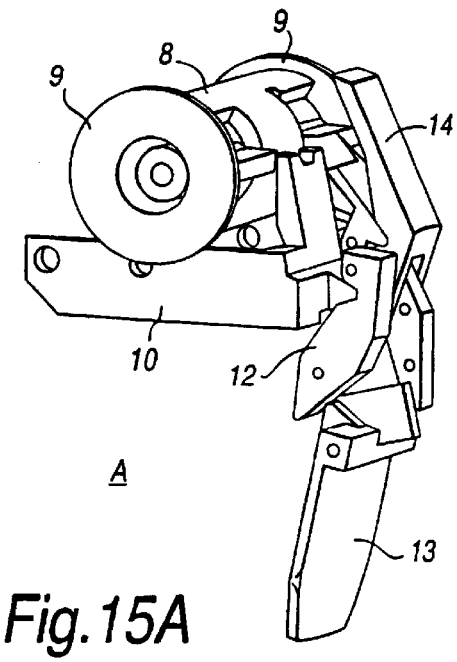
FIGS. 15 to 22 are views of the actuation mechanism in various states during its operation sequence with views from opposite sides being suffixed by the letters A, B respectively.
Figure 15B:
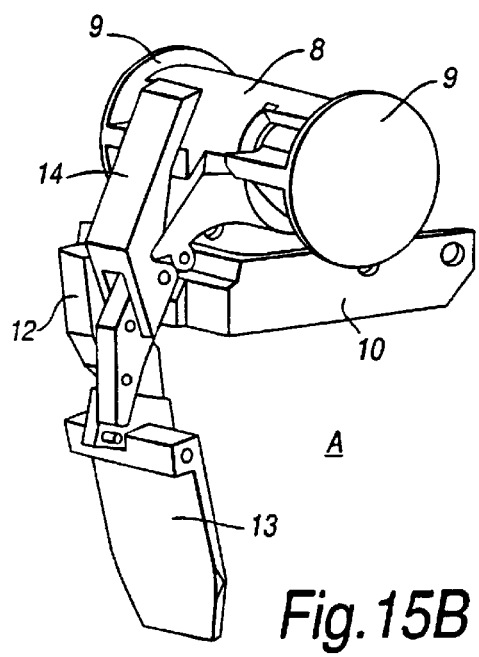
Figure 16A:
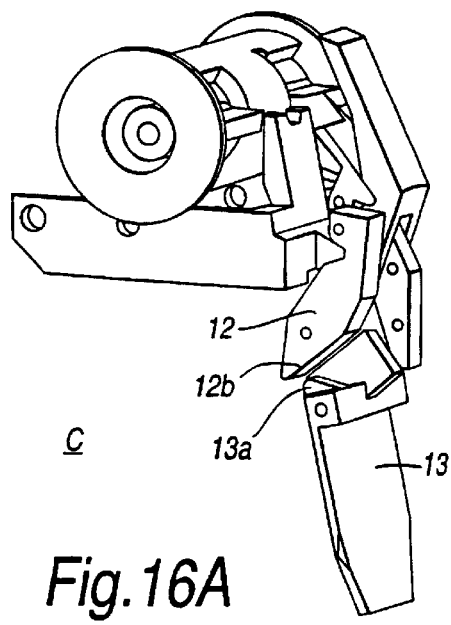
Figure 16B:
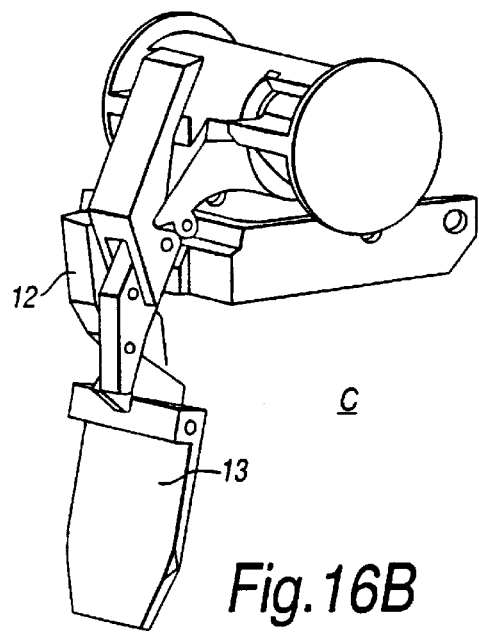
Figure 17A:
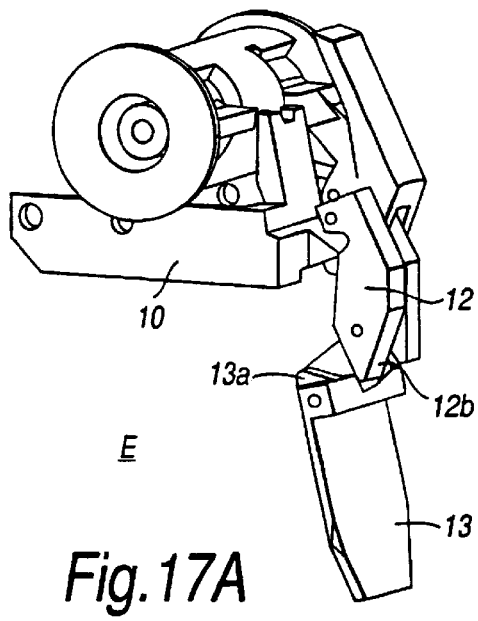
Figure 17B:
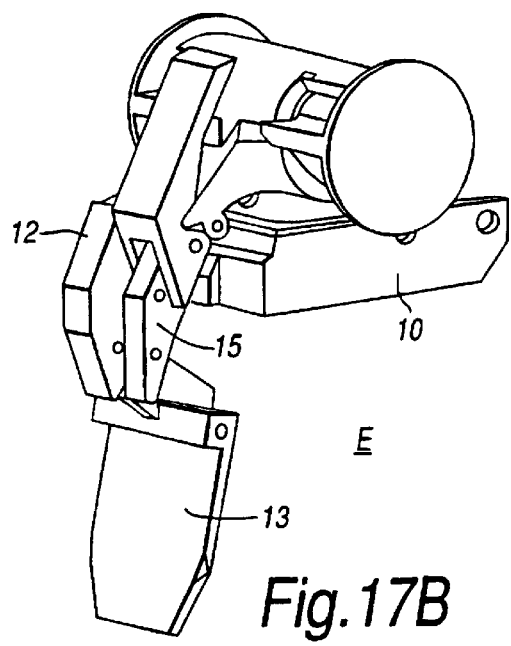
Figure 18A:
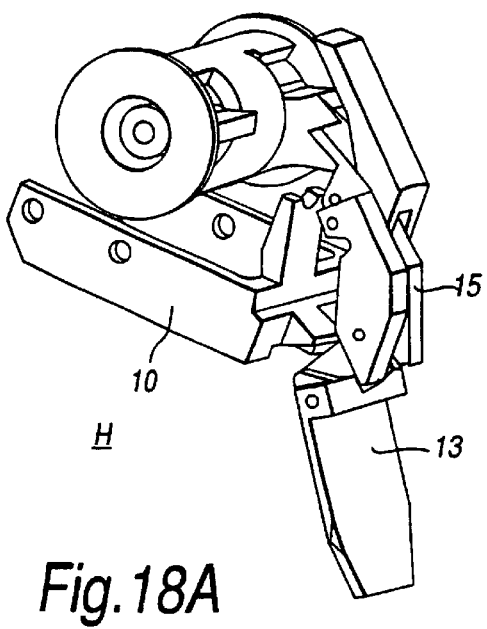
Figure 18B:
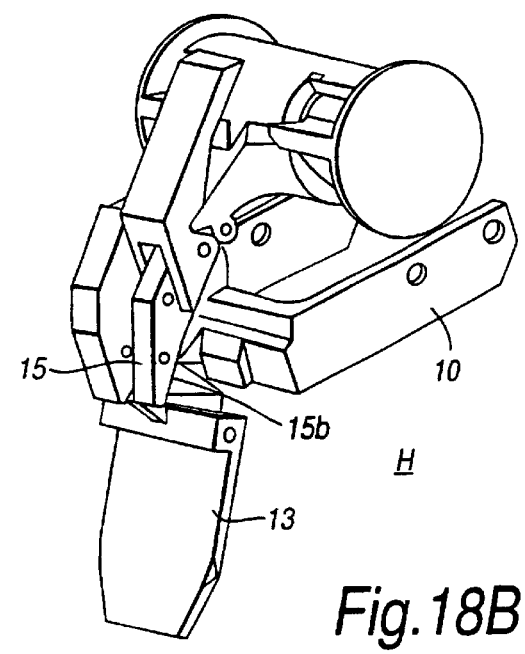
Figure 19A:
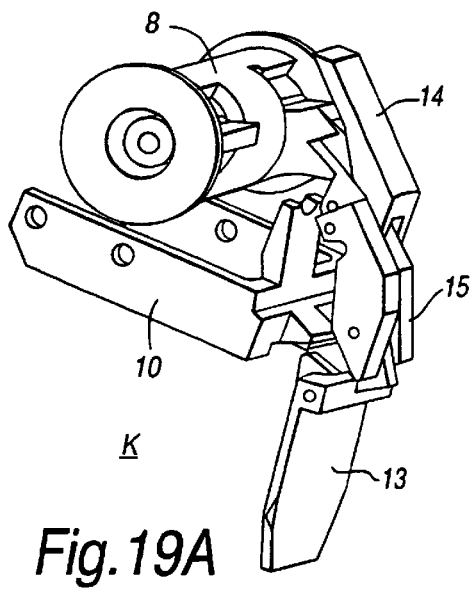
Figure 19B:
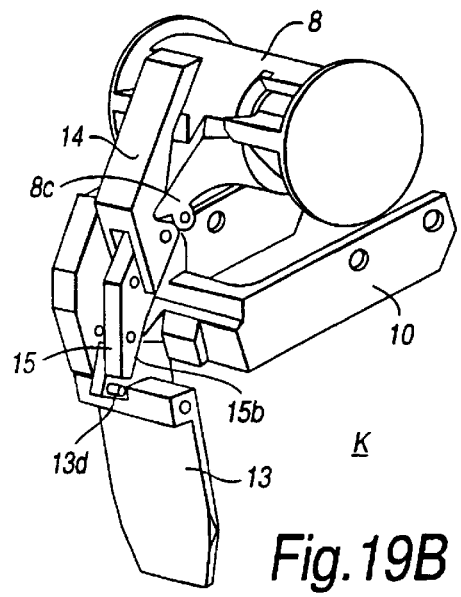
Figure 20A:
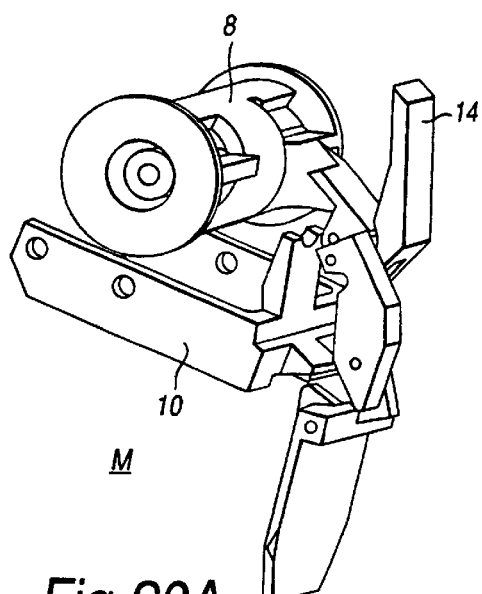
Figure 20B:
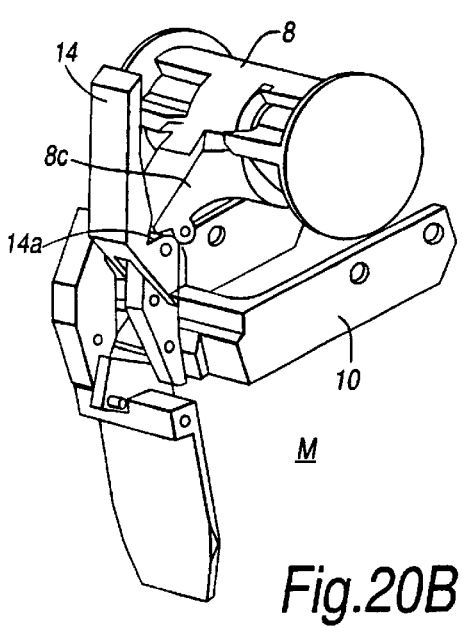
Figure 21A:
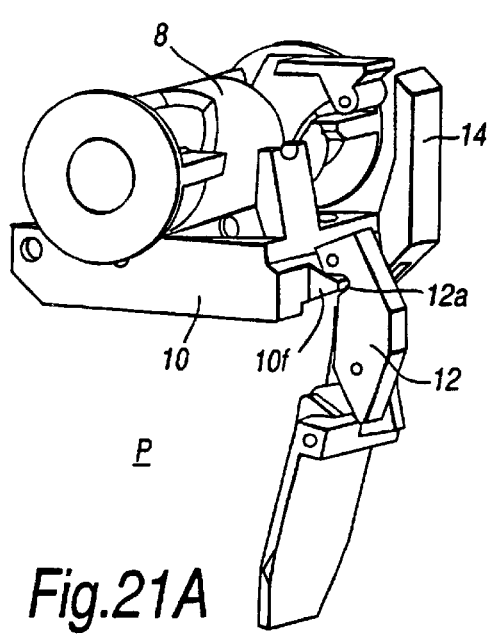
Figure 21B:
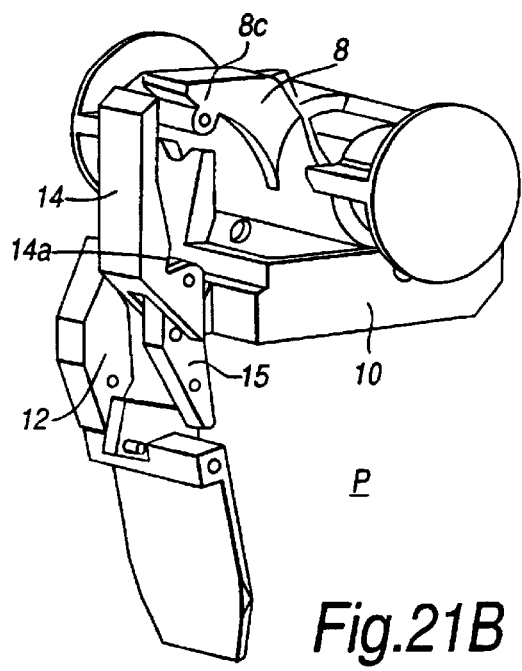
Figure 22A:
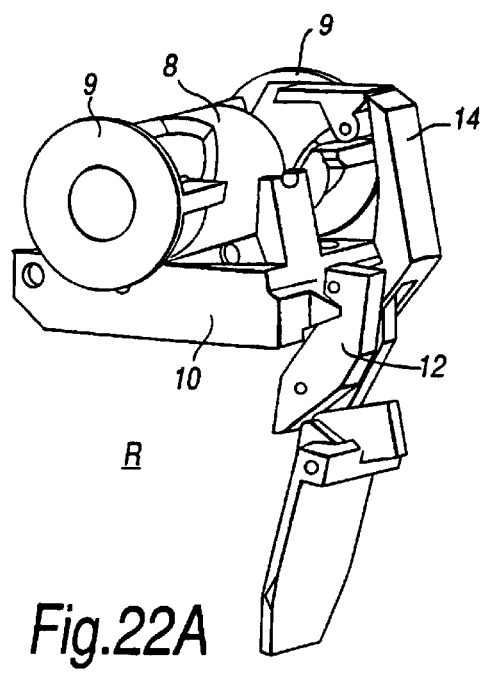
Figure 22B:
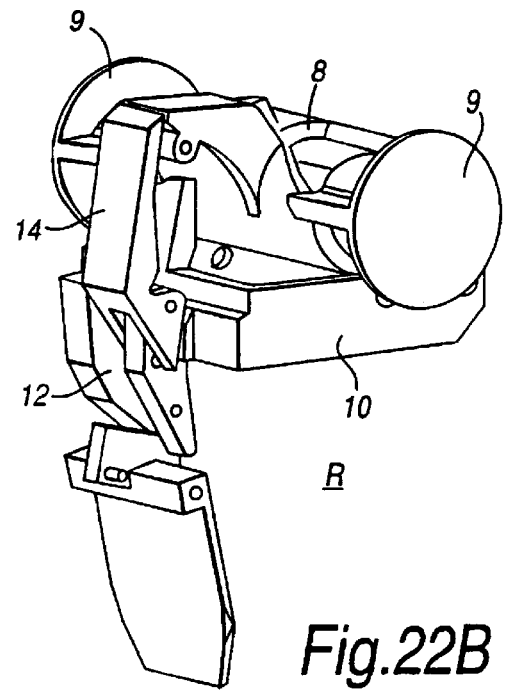

The sequence commences in state A as shown in FIG. 15 in which the torsion spring 7 has been loaded by depression of the buttons 9 and the spindle 8 is locked by the catch 14. In state A, the canister engagement lever is 10 held by the locking lever 12. The inhaler may be stored with the actuation mechanism 6 in state A.

At position B, the user starts to inhale. The flap 13, being responsive to such inhalation, starts to move. The shape of the contact surface 12b allows the locking lever 12 to start moving slowly. The actuation mechanism 6 is now in state C illustrated in FIG. 16.

At position D, the locking lever engagement surface 13a of the flap 13 releases the contact surface 12b of the locking lever 12. Accordingly, the canister engagement member 10 under the loading of the torsion spring 7 starts to rotate downwards deflecting the locking lever 12 against its reset spring as the projection 10f moves out of the notch 12a. The actuation mechanism is now in state E illustrated in FIG. 17.

At position F, the canister engagement lever 10 moves out of contact with the first contact surface 15a at the intermediate member 15 which therefore starts to move under the biassing of spring 16. However, the intermediate member 15 only moves a short way because at position G it is caught by the flap 13, in particular by the bar 13d of the flap 13 contacting the second contact surface 15b. This contact stops the movement of the flap 13 and the intermediate member 15.

The movement of the canister engagement lever 10 compresses the body 3 of the canister 2 relative to the stem 4 held in the nozzle block 11, thereby causing the canister 2 to deliver a dose of medicament. The nozzle block 11 directs the dose of medicament out of the mouthpiece at which the user is inhaling. The actuation mechanism 6 is now in state H illustrated in FIG. 18.

When the level of inhalation starts to fall, at position I the flap 13 under the biassing of its reset spring starts to move back closing the duct. This movement of the flap 13 causes the intermediate member 15 to move slightly due to the shape of the second contact surface 15b.

When the level of inhalation falls below the predetermined threshold, at position J the bar 13d of the flap 13 moves out of contact with the second contact surface 15b. This releases the intermediate member 15. Under the action of the spring 16, the intermediate member 15 moves to unload the spring 16. The actuation mechanism 6 is now in state K illustrated in FIG. 19.

At position L the load on the catch 14 from the spring 16 reduces to the extent that the catch 15 can no longer hold the spindle 8. The force of the torsion spring 7 forces the arm 8c of the spindle 8 upwards and out of engagement with the notch 14a of the catch 14. This forces the catch 14 backwards. The actuation mechanism 6 is now in state M illustrated in FIG. 20.

At position N, the torsion spring 7 reaches its neutral, unloaded position, so there is no load between the canister engagement lever 10 and the spindle 8. Thereafter the canister engagement lever 10 and the torsion spring 8 are moved under the action of the reset spring biassing the canister engagement lever 10.

At position O, the canister engagement lever 10 contacts the first contact surface 15a of the intermediate member 15 and forces it backwards. The actuation mechanism is now in state P illustrated in FIG. 21. This loads the spring 16 and pushes the catch 14 towards its locking position until the catch 14 contacts the arm 8c of the spindle 8 which has now passed out of the notch 14a.

At position Q, the projection 10f of the canister engagement lever 10 moves into the notch 12a of the locking lever 12 which snaps back into its locking position under the action of its reset spring. The actuation mechanism 6 is now in state R in FIG. 22. In state R, the canister is reset and ready to be compressed again for delivery of the next dose, but the actuation mechanism 6 is relaxed with the torsion spring 7 unloaded. The rotation of the spindle 8 has forced the buttons 9 outwards to the position illustrated in FIG. 22. The actuation mechanism 6 is ready to be loaded once again by compression of the buttons 9. The user is instructed to do this immediately after inhalation, so that the canister may be stored in a state ready to be used simply by inhaling at the mouthpiece 5.

When the user depresses the buttons 9 at position S, this drives the spindle 8 downwards. The arm 8c of the spindle 8 deflects the catch 14 slightly against the loaded spring 16 until the arm 8c moves into the notch 14a. This allows the spring 16 to snap the catch 14 into its locking position.

Figure 23:
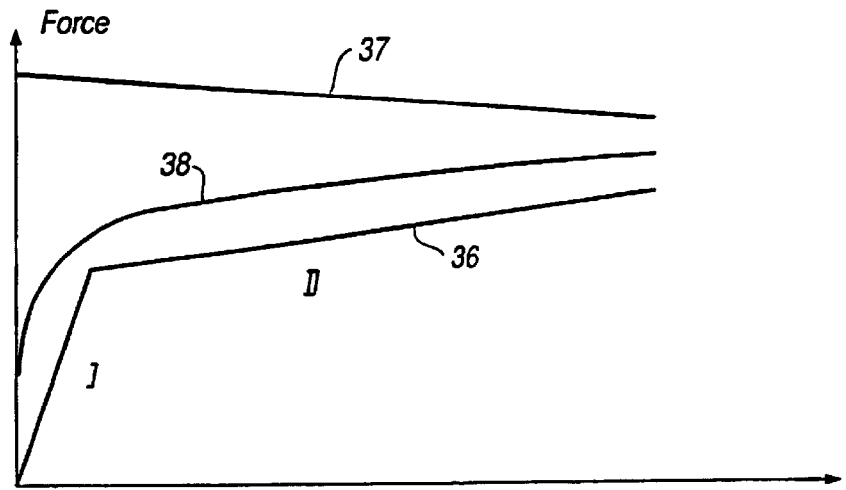
FIG. 23 is a graph showing forces generating during the compression stroke of the canister.

FIG. 23 shows various forces generated during the compression stroke of the canister 2 after the canister engagement lever 10 has been released by the triggering mechanism.

The resistive force generated by the canister 2 is illustrated by line 36. This has two phases. In the first phase I, the resistive force rises steeply because it is derived from both compression of the internal valve spring and compression of gaskets in the canister 2 resulting in a large overall spring constant. In the second phase II, the resistive force rises more gently, because the gaskets cease to have an effect so the spring constant is derived solely from the compression of the internal valve spring.

It is essential that the force applied to the canister exceeds the resistive force or else the canister 2 will cease to be compressed. The force applied by the torsion spring 7 will decrease as it expands over the compression stroke of the canister 2, typically linearly. Therefore, the torsion spring 7 is selected so that the force generated, as shown by line 37 in FIG. 23, exceeds the force required to compress the canister 2 at the end of the compression stroke, which is where the resistive force is greatest. The force applied by the torsion spring 7 is higher still at the beginning of the compression stroke in which state the torsion spring 7 is held when the device is loaded. This high force can create creep in the parts holding the torsion spring in its compressed state when the parts are made of plastic which is desirable to simplify manufacture and reduce costs. In particular, those parts are the canister engagement lever 10 and lever 12 of the triggering mechanism which hold the lever 10 against compression of the canister 2 and also the spindle 8 and catch 14 of the locking mechanism which locks the spindle 8 after loading of the torsion spring 7.

It has been appreciated that it is possible to provide a linkage between the torsion spring 7 and the canister engagement member 10 to reduce the force applied by the canister engagement member 10 of the triggering mechanism in the loaded state. Some possible linkages which may be introduced as modifications to the actuation mechanism described above with reference to FIGS. 7 to 22 are described below.

Figure 24A:
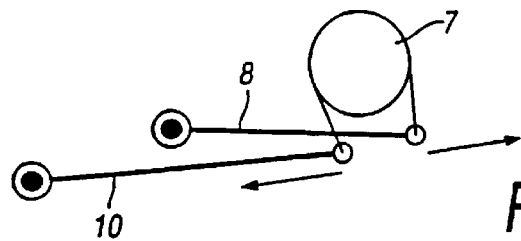
FIGS. 24A to 24C are views of an alternative arrangement for the torsion spring.
Figure 24B:
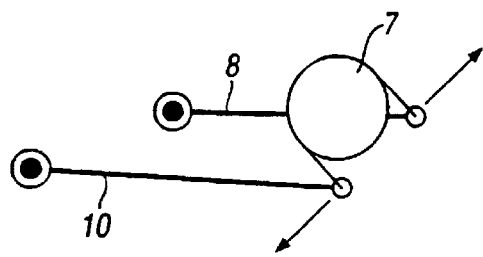
Figure 24C:
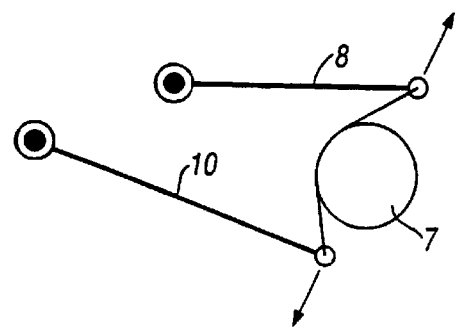

A first linkage is illustrated in FIGS. 24A to 24C in which the canister engagement member 10 and the spindle 8 are illustrated schematically. In this arrangement, the torsion spring 7 is pivotally connected to the ends of the canister engagement member 10 and the spindle 8 and the torsion spring 7 is freely suspended so is free to move without its coils being restrained as occurs in the structure of FIG. 7 because the torsion spring 7 is mounted on the spindle 8.

The torsion spring 7 has linear characteristics, but is arranged so that in the loaded state of the device shown in FIG. 24A, the force applied by the torsion spring acts in a direction at a very narrow angle to the canister engagement lever 10, (or more precisely to the line between the axis of rotation of the canister engagement lever 10, and its pivotal connection with the torsion spring 7). Therefore, a large component of the force applied by the torsion spring 7 is applied through the bearing of the canister engagement lever 10 and only a small component of this force creates a torque tending to rotate the canister engagement lever 10. Therefore, the force applied by the canister engagement lever 10 to the locking lever 12 is reduced. Similarly the force applied to the torsion spring 7 to the spindle 8 also acts at an oblique angle to the line between the axis of rotation of the spindle 8 of the pivotal connection between the spindle 8 and torsion spring 7. This reduces the component of that force tending to rotate the spindle 8.

After the canister engagement lever 10 is released by the locking lever 12, the torsion spring 7 causes the canister engagement lever 10 to rotate downwardly as illustrated in FIGS. 24B and 24C. As the canister engagement lever 10 rotates, it draws the torsion spring 7 down and changes the orientation of the torsion spring 7. Consequently the torsion spring 7 applies a force to the canister engagement lever 10 at a steadily increasing angle to the canister engagement lever 10. Therefore, the component of the force on the torsion spring 7 which creates a torque to rotate the canister engagement lever 10 rises, whereby the force applied to the canister 2 also rises.

In this way, it is possible to control the force applied by the torsion spring 7 to the canister 2 to be at the level shown by the line 38 in FIG. 23. It will be seen the applied force 38 always exceeds the resistive force generated by the canister 2 which is necessary to compress the canister 2. Nonetheless the linkage limits the force 38 when the actuation mechanism 6 is loaded ready for use, because the bearings carry this load of the canister engagement member 10.

Figure 25:
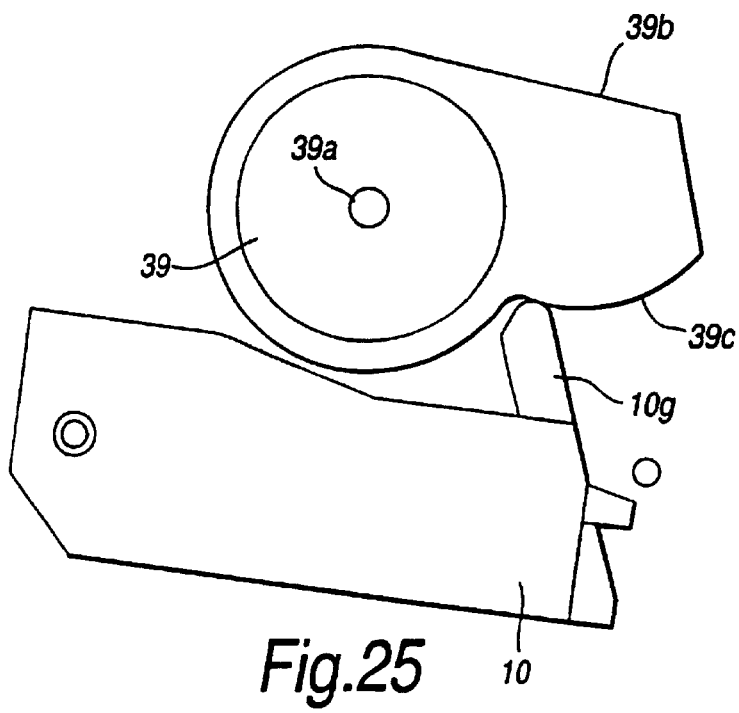
FIGS. 25 and 26 are views of an alternative linkage between the torsion spring and the canister engagement lever.
Figure 26:
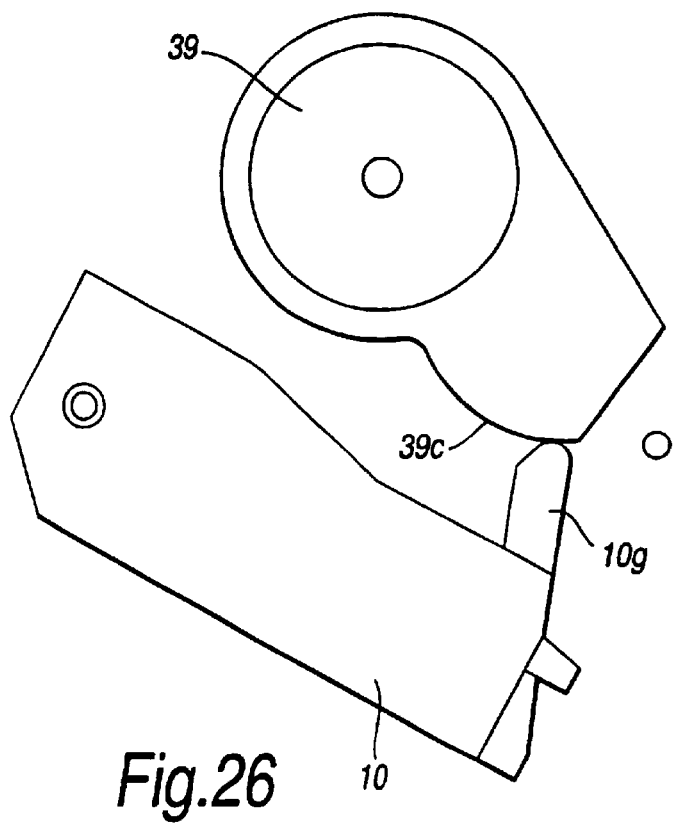

A second possible linkage is illustrated in FIGS. 25 and 26 in which an intermediate member 39 is provided between the torsion spring 7 and the canister engagement lever 10. The intermediate member 39 is pivotally mounted to the interior of the housing about an axis 39a. The torsion spring 7 engages the upper surface 39b of the intermediate member 39a for downward biassing. The intermediate member 39 and the canister engagement lever 10 engage one another through a cam arrangement which consists of a cam surface 39c on the lower surface of the intermediate member 39 and a cam follower 10 g protruding upwardly from the canister engagement lever 10. The shape of the cam surface 39c controls the force applied to the canister engagement lever 10. In particular, the cam surface is arranged to reduce this force in the loaded state illustrated in FIG. 25. After the canister engagement lever 10 is released by the locking lever 12, it rotates as illustrated in FIG. 26 and the force applied to the canister engagement lever 10 increases. By appropriately shaping the cam surface 39c it is possible to generate any desired force profile.

What is claimed is:

1. An inhaler for delivery of medicament from a canister which is compressible to deliver a dose of medicament, the inhaler comprising:

a housing for holding a canister;

a canister engagement member engageable with a canister held in the housing to compress the canister;

a loading mechanism for loading a resilient loading element which is arranged, when loaded, to bias the canister engagement member to compress the canister;

a triggering mechanism arranged to hold the canister engagement member against compression of the canister and triggerable to release the canister engagement member, and a linkage between the resilient loading element and the canister engagement member, wherein the linkage between the resilient loading element and the canister engagement member is arranged to reduce the force applied by the canister engagement member to the triggering mechanism when held by the triggering mechanism.

2. An inhaler according to claim 1, said resilient loading element is pivotally connected to said canister engagement member.

3. An inhaler according to claim 1, wherein said resilient loading element is a torsion spring.

4. An inhaler according to claim 3, wherein said torsion spring is freely suspended.

5. An inhaler according to claim 1, wherein the loading mechanism drives a loading member coupled to the resilient loading element to load the resilient loading element and further comprises a locking mechanism arranged to hold the loading element in a loaded state; and the resilient loading element is pivotally connected to said loading member.

6. An inhaler according to claim 1, wherein the said linkage includes a cam arrangement for reducing said force.

7. An inhaler according to claim 6, wherein said linkage includes an intermediate member biassed by said resilient loading element, when loaded, to engage the canister engagement member, said cam arrangement being provided between the intermediate member and the canister engagement member.

8. An inhaler according to claim 7, wherein said intermediate member is rotatable.

9. An inhaler according to claim 7, wherein said canister engagement member is rotatable.

10. An inhaler according to claim 7, wherein said cam arrangement consists of a cam surface provided on said intermediate member and a cam follower provided on said canister engagement member.

11. An inhaler according to claim 1, wherein said canister engagement member has a stroke, and said linkage includes:

an intermediate member biased by said resilient loading element, when loaded, to engage the canister engagement member; and a mechanical linkage between the canister engagement member and the intermediate member arranged to provide said reduction in the force at the beginning of the stroke of the canister engagement member.

12. An inhaler for delivery of medicament from a canister which is compressible to deliver a dose of medicament, the inhaler comprising:

a housing for holding a canister;

a loading mechanism for loading a resilient loading element which is arranged, when loaded, to bias compression of the canister;

a triggering mechanism arranged to hold the resilient loading element against compression of the canister and triggerable to release the resilient loading element, and a linkage between the resilient loading element and the triggering mechanism wherein the linkage between the resilient loading element and the triggering mechanism is arranged to reduce the force applied by the resilient loading element to the triggering mechanism when held by the triggering mechanism.

13. An inhaler according to claim 12, wherein the said linkage includes a cam arrangement for reducing said force.

14. An inhaler according to claim 13, wherein said linkage includes:

a canister engagement member engageable with a canister held in the housing to compress the canister, the triggering mechanism engaging the canister engagement member;

an intermediate member biassed by said resilient loading element, when loaded, to engage the canister engagement member, said cam arrangement being provided between the intermediate member and the canister engagement member.

15. An inhaler according to claim 14, wherein said intermediate member is rotatable.

16. An inhaler according to claim 14, wherein said canister engagement member is rotatable.

17. An inhaler according to claim 14, wherein said cam arrangement consists of a cam surface provided on said intermediate member and a cam follower provided on said canister engagement member.

18. An inhaler according to claim 12, wherein said linkage includes:

a canister engagement member engageable with a canister held in the housing to compress the canister, the triggering mechanism engaging the canister engagement member;

an intermediate member biassed by said resilient loading element, when loaded, to engage the canister engagement member; and a mechanical linkage between the canister engagement member and the intermediate member arranged to provide said reduction in the force at the beginning of the stroke of the canister engagement member.

* * * * *